US00PP28214P3

(12) United States Plant Patent
Olesen

(10) Patent No.: US PP28,214 P3
(45) Date of Patent: Jul. 25, 2017

(54) ROSE PLANT NAMED 'POULPAH076'

(50) Latin Name: ***Rosa* hybrid**
Varietal Denomination: Poulpah076

(71) Applicant: Mogens Nyegaard Olesen, Fredensborg (DK)

(72) Inventor: Mogens Nyegaard Olesen, Fredensborg (DK)

(73) Assignee: Poulsen Roser A/S, Fredensborg (DK)

( * ) Notice: Subject to any disclaimer, the term of this patent is extended or adjusted under 35 U.S.C. 154(b) by 0 days.

(21) Appl. No.: 14/756,270

(22) Filed: Aug. 20, 2015

(65) Prior Publication Data

US 2017/0055390 P1 Feb. 23, 2017

(51) Int. Cl.
*A01H 5/02* (2006.01)

(52) U.S. Cl.
USPC ..... Plt./121

(58) Field of Classification Search
USPC ..... Plt./121, 128
CPC ..... A01H 5/0222
See application file for complete search history.

(56) References Cited

PUBLICATIONS http://www.poulsenroser.com/media/73602/PATIOHIT-Outdoor-2013_LR_Poulsen-Roser.pdf; 2012, 1 page.*

* cited by examiner

*Primary Examiner* — Kent L Bell

(57) ABSTRACT

A new garden rose plant of the miniature class which has abundant, pink flowers and attractive foliage. This new and distinct variety has shown to be uniform and stable in the resulting generations from asexual propagation.

2 Drawing Sheets

Botanical designation: *Rosa* hybrid.
Variety denomination: 'Poulpah076'.

SUMMARY OF THE INVENTION

The present invention constitutes a new and distinct variety of garden rose plant which originated from a controlled crossing between the female seed parent, an unnamed seedling, and the male pollen parent, also an unnamed seedling. Both of the parent varieties are non-patented.

The two parents were crossed during the summer of 2008 and the resulting seeds were planted in a controlled environment in Fredensborg, Denmark. The new variety, named 'Poulpah076', originated as a single seedling from the stated cross.

The new variety may be distinguished from its male pollen parent and female seed parent primarily by the following characteristics. The female seed parent has light red flowers while the new variety has pink flowers. The male pollen plant has flowers which are Red-Purple Group 63C, while the new variety has flowers which are Red-Purple Group N57C.

The objective of the hybridization of this rose variety was to create a new and distinct variety for garden use with unique qualities, such as:

1. Uniform and abundant pink flowers;
2. Vigorous, but compact growth when propagated both as a budded rose and on its own roots;
3. Exceptional disease resistance.

This combination of qualities is not present in previously available commercial cultivars of this type, known to the inventor, and distinguish 'Poulpah076' from all other varieties of which we are aware.

As part of the rose development program, Mogens N. Olesen germinated the seeds from the aforementioned hybridization during winter of 2008 and conducted evaluations on the resulting seedlings in a controlled environment in Fredensborg, Denmark. 'Poulpah076' was selected in the spring of 2009 by the inventor as a single plant from the progeny of the aforementioned hybridization.

Asexual reproduction of 'Poulpah076' by traditional budding and rooted cuttings was first done by Mogens N. Olesen in the nursery in Fredensborg, Denmark in July, 2009. This initial and other subsequent asexual propagations conducted in controlled environments have demonstrated that the characteristics of 'Poulpah076' are true to type and are transmitted from one generation to the next.

DESCRIPTION OF THE DRAWING

The accompanying color illustrations show as true as is reasonably possible to obtain in color photographs of this type, the typical characteristics of the buds, flowers, leaves, and stems, of 'Poulpah076'.

Specifically illustrated in FIG. 1 of the drawings are a cluster of open flowers, flower petals detached, sepals detached, and reproductive flower parts.

Figure 1:
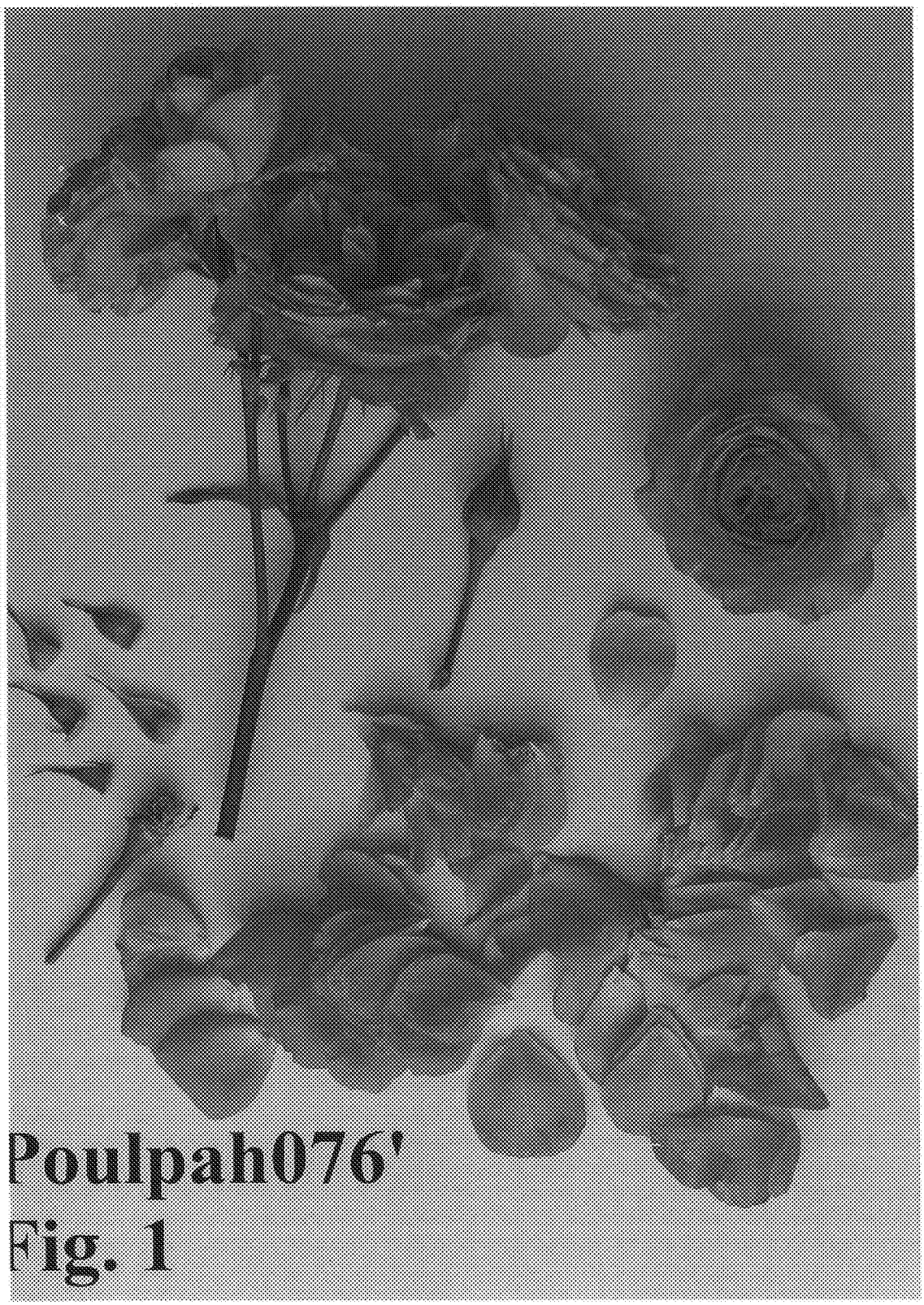
Figure 2:
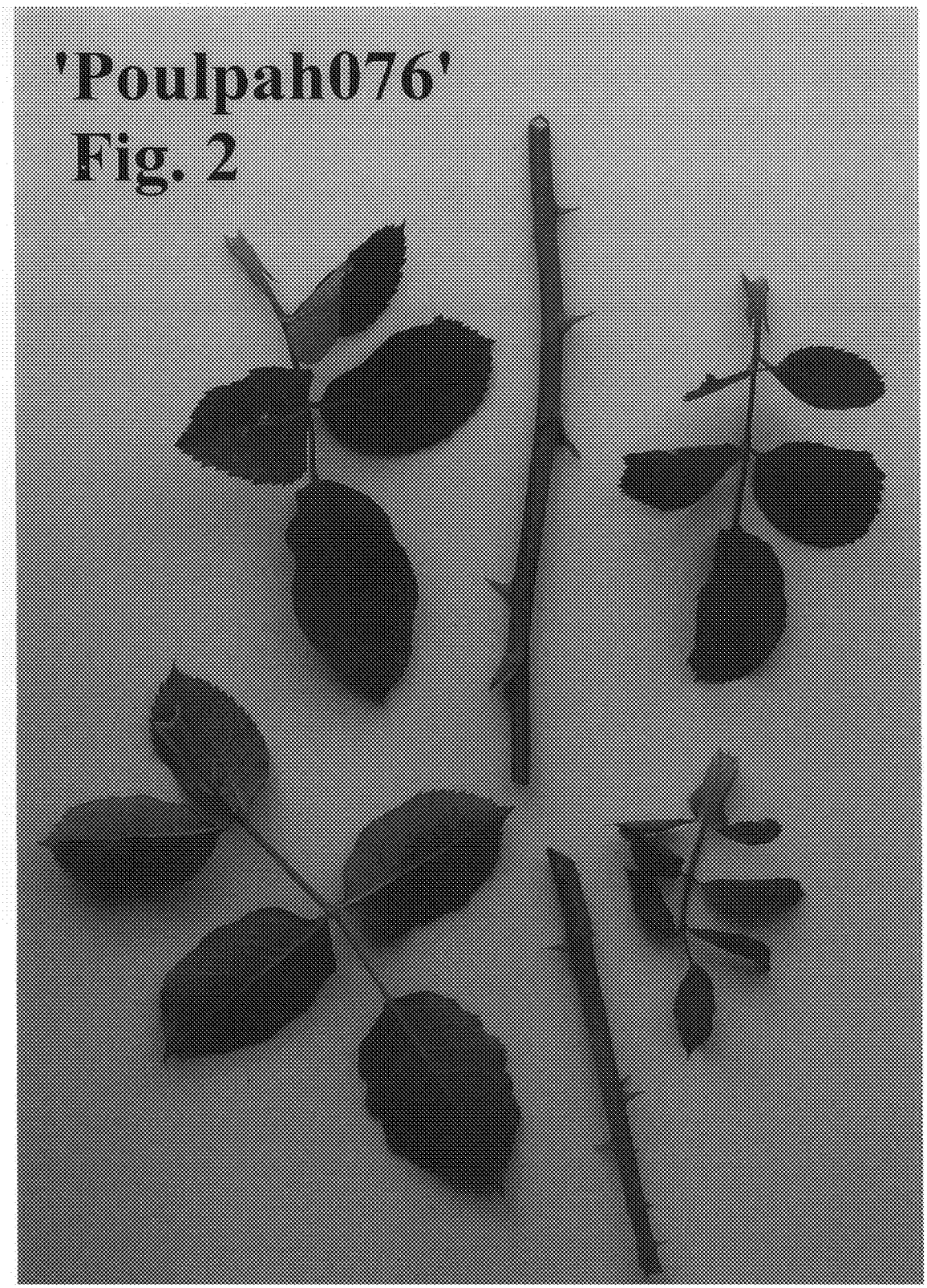

Specifically illustrated in FIG. 2 of the drawings are mature and juvenile leaves, mature and juvenile stems.

Plants shown are 2 years of age.

DETAILED DESCRIPTION OF THE VARIETY

The following is a description of 'Poulpah076', as observed in its growth in a field nursery in Marion County, Oreg. Observed plants are 2 years of age, and were grown on their own roots. Color references are made using The Royal Horticultural Society (London, England) Colour Chart, 2001, except where common terms of color are used.

For a comparison, several physical characteristics of the rose variety 'Poultin', U.S. Plant Pat. No. 10,164 are compared to 'Poulpah076' in the chart named Comparison with Comparative cultivar 'Poultin'.

CHART 1

| | 'Poulpah076' | 'Poultin' |
|---|---|---|
| Petal Count | 100 | 20-25 |
| Upper petal color | Red-Purple Group N57C | Red Purple Group 58B |

Flower and Flower Bud

Blooming habit: Continuous.

Flower bud:

*Size.*—Upon opening, 30 mm in length from base of receptacle to end of bud. Bud diameter is 17 mm.

*Bud form.*—Ovoid.

*Bud color.*—As sepals divide petals are Red-Purple Group N66B.

*Sepal inner surface.*—Color: Yellow-Green Group 145C. Surface: Lightly pubescent.

*Sepal outer surface.*—Color: Yellow-Green Group 144A. Texture: Smooth.

*Sepal shape.*—Apex: Cirrhose. Base: Flat at union with receptacle.

*Sepal margin.*—Margins have weak foliaceous appendages on three of the five sepals.

*Sepal size.*—32 mm long, 10 mm wide.

*Receptacle.*—Texture: Smooth. Size: 9 mm in height, 8 mm wide. Color: Yellow-Green Group 144A. Shape: Campanulate.

*Pedicel.*—Surface: Smooth. Length: About 45 mm. Diameter: 3 mm on average. Color: Yellow-Green Group 144A. Strength: Strong.

*Peduncle.*—Length: 3 to 4 cm. Diameter: About 3.5 mm. Color: Yellow-Green Group 145A. Texture: Smooth.

Flower bud development: Flower buds are borne in corymbs of 5 to 7 flower buds per stem.

Flower bloom:

*Fragrance.*—Moderate perfume.

*Duration.*—The blooms have a duration on the plant of approximately 15 days. Petals fall cleanly away from plant after flowers have fully matured.

*Size.*—Flower diameter is 85 mm when open. Flower depth is 30 mm.

*Flower shape.*—Quartered-rosette, very double, with many overlapping petals packed into quarter sections.

*Shape of flower, side view.*—The upper portion is flat. The lower portion is concave.

Petalage: Under normal conditions, flowers have 100 petals total, 10 of which are petaloids.

General tonality of flower: Open flowers are Red-Purple Group N57C.

Petal color:

*Upon opening, inner and outer petals.*—Upper surface: Red-Purple Group N57C. Lower surface: Red-Purple Group N66C splashed with Yellow Group 8D.

*Basal petal spots, upon opening.*—Upper surface: Yellow Group 8D. Lower surface: Yellow Group 8D.

*After opening, inner and outer petals.*—Upper surface: Red-Purple Group N57C. Lower surface: Red-Purple Group N66C splashed with Yellow Group 8D.

*Basal petal spots, after opening.*—Upper surface: Yellow Group 8D. Lower surface: Yellow Group 8D.

Petals:

*Petal reflex.*—Flat.

*Margin.*—Point at the apex. Moderate to strong undulations.

*Shape.*—Generally rounded. Apex shape: Rounded. Base shape: Acute.

*Size.*—40 mm (l)×40 mm (w).

*Texture.*—Smooth.

*Thickness.*—Average.

Petaloids:

*Size.*—25 mm (l) by 11 mm (w).

*Quantity.*—About 10.

*Shape.*—Irregular.

*Color.*—Upper surface is Red-Purple Group N57C with petal spot of Yellow Group 8D. Lower surface is Red-Purple Group N66C splashed with Yellow Group 8D beginning at the base.

Reproductive flower parts:

*Pollen.*—None observed.

*Anthers.*—Size: 2 mm in length. Color: Yellow Group 11B. Quantity: 25 on average.

*Filaments.*—Color: Yellow Group 11A. Length: 3 mm.

*Pistils.*—Length: 4 mm. Quantity: 30 on average.

*Stigmas.*—Color: Greyed-Yellow Group 162B.

*Styles.*—Color: Red-Purple Group N66B.

*Location of stigmas.*—Superior in location relative to the length of the filaments and the height of the anthers.

*Hips.*—None Observed.

Plant

Plant growth: Upright, bushy. Plants are 45 cm in height, and 45 cm wide.

Stems:

*Color.*—Juvenile growth: Yellow-Green Group 144B. Mature growth: Yellow-Green Group 144A.

*Length.*—On average, canes are 25 cm from the base of the plant to the flowering portion.

*Diameter.*—About 5 mm.

*Internodes.*—On mature canes about 60 mm between nodes.

*Surface texture.*—Young wood: Smooth. Older wood: Smooth.

Long prickles:

*Incidence.*—3 prickles per 10 cm of stem.

*Size.*—Average length of prickles on mature stems is 10 mm.

*Shape.*—Upper portion is linear. Lower portion is concave.

*Color.*—Juvenile prickles: Greyed-Orange Group 171C. Mature prickles: Yellow-Green Group 153D.

Plant foliage:

*Compound leaf.*—155 mm (l)×110 (w).

*Quantity.*—2 leaves per 10 cm of stem on average.

*Color of juvenile foliage*.—Upper side: Yellow-Green Group 144A. Lower side: Yellow-Green Group 144A. Anthocyanin: Greyed-Red Group 180A at margins.

*Color of mature foliage*.—Upper side: Yellow-Green Group 146A. Lower side: Yellow-Green Group 146B.

Plant leaves and leaflets:

*Stipules*.—Size: 25 mm long, 10 mm wide. Quantity: 2 per compound leaf. Shape: Linear, slightly broad based with outward extending apices. Margins: Finely serrated. Color: Yellow-Green Group 144A.

*Petiole*.—Length: 30 mm. Diameter: 1.5 mm.

*Upper surface*.—Color: Yellow-Green Group 144A.

*Lower surface*.—Color: Yellow-Green Group 144A.

*Rachis*.—Length: 60 mm. Upper surface: Color: Yellow-Green Group 144A. Lower surface: Color: Yellow-Green Group 144A. Observations: Small prickles.

*Leaflet*.—Quantity: Normally 5 leaflets. Margins: Serrated. Size: On average terminal leaflets are 60 mm long, 40 mm wide. Shape: Generally elliptical. Base: Rounded. Apex: Mucronate. Texture: Smooth. Thickness: Average. Arrangement: Odd pinnate. Venation: Reticulate. Glossiness: Very glossy.

Disease resistance: Above average resistance to powdery mildew *Sphaerotheca pannosa*, downy mildew *Peronospora sparsa*, rust *Phragmidium* sps., black spot *Diplocarpon rosae*, and *Botrytis cinerea* under normal growing conditions.

Cold hardiness: The variety is tolerant to USDA Cold Hardiness Zone 6.

Heat tolerance: The variety has been found to be suitable for climate conditions found in the American Horticulture Society heat zone 7.

I claim:

1. A new and distinct variety of rose plant of the miniature rose class named 'Poulpah076', substantially as illustrated and described herein, due to its abundant pink flowers, disease resistance, and extended period of bloom.

* * * * *

Poulpah076'

'Poulpah076'